United States Patent
Liu et al.

(10) Patent No.: US 11,857,490 B2
(45) Date of Patent: Jan. 2, 2024

(54) NEGATIVE-PRESSURE CUP STRUCTURE WITH VIBRATION MECHANISM

(71) Applicant: BIBOTING INTERNATIONAL CO., LTD., Taoyuan (TW)

(72) Inventors: Po-Chang Liu, Taoyuan (TW); Chia-Hsueh Hsieh, Taoyuan (TW); Li-Pin Yuan, Taoyuan (TW)

(73) Assignee: BIBOTING INTERNATIONAL CO., LTD., Taoyuan (TW)

( * ) Notice: Subject to any disclaimer, the term of this patent is extended or adjusted under 35 U.S.C. 154(b) by 282 days.

(21) Appl. No.: 17/412,067

(22) Filed: Aug. 25, 2021

(65) Prior Publication Data

US 2023/0069573 A1   Mar. 2, 2023

(51) Int. Cl.
*A61H 9/00* (2006.01)
*A61H 23/02* (2006.01)
*A61M 1/08* (2006.01)

(52) U.S. Cl.
CPC ......... *A61H 9/0057* (2013.01); *A61H 9/0007* (2013.01); *A61H 23/02* (2013.01); *A61M 1/08* (2013.01)

(58) Field of Classification Search
CPC .... A61H 9/0057; A61H 9/0007; A61H 23/02; A61H 23/00; A61H 9/00; A61H 9/005; A61M 1/08; A61M 2205/05; A61M 2205/106
USPC ...................................................... 601/6, 15
See application file for complete search history.

(56) References Cited

U.S. PATENT DOCUMENTS

| | | | | |
|---|---|---|---|---|
| 5,902,293 | A * | 5/1999 | Liu ........................ | A61H 9/005 604/74 |
| 2002/0188231 | A1 * | 12/2002 | Liu ...................... | A61H 9/0057 601/6 |
| 2008/0106896 | A1 * | 5/2008 | Liu ...................... | A61H 9/0057 362/234 |
| 2009/0299234 | A1 * | 12/2009 | Cho ..................... | A61H 9/0057 601/2 |
| 2018/0339090 | A1 * | 11/2018 | Santana ................. | A61M 1/08 |
| 2020/0390948 | A1 * | 12/2020 | Liu ...................... | A61H 9/0057 |
| 2021/0038466 | A1 * | 2/2021 | Stewart, Jr. .......... | A61N 1/0472 |

(Continued)

FOREIGN PATENT DOCUMENTS

CN          115518217 A  * 12/2022
WO    WO-2022035753 A1 *  2/2022

*Primary Examiner* — Tu A Vo
*Assistant Examiner* — Kelsey E Baller
(74) *Attorney, Agent, or Firm* — Chun-Ming Shih; HDLS IPR SERVICES

(57) ABSTRACT

A negative-pressure cup structure includes a cup and a vibration generating mechanism. The cup has a chamber. Two ends of the cup are separately formed with an opening end and a closed end. The closed end is provided with a negative-pressure suction hole and an electric connection hole communicating with the chamber. A bar is extended from the closed end and located in the chamber. The vibration generating mechanism includes a box, a vibration member disposed in the box and a power connector electrically connected to the vibration member. The vibration generating mechanism is fixed in the chamber of the cup in a manner of the box and the bar being connected and the power connector being inserted to the electric connection hole. Therefore, the users may obtain a better vibrational sense.

10 Claims, 5 Drawing Sheets

(56) References Cited

U.S. PATENT DOCUMENTS

| | | | |
|---|---|---|---|
| 2021/0187287 A1* | 6/2021 | Bezalel | A61N 1/327 |
| 2022/0054779 A1* | 2/2022 | Bogan | A61M 15/0013 |
| 2022/0313538 A1* | 10/2022 | Solana | A61H 7/008 |
| 2022/0387678 A1* | 12/2022 | Park | A61M 1/80 |

* cited by examiner

NEGATIVE-PRESSURE CUP STRUCTURE WITH VIBRATION MECHANISM

BACKGROUND

Technical Field

The disclosure relates to a negative-pressure cup structure, particularly to a negative-pressure cup structure with a vibration mechanism.

Related Art

A negative-pressure cup is a healthcare gear which covers human skin and utilizes negative-pressure suction to stimulate skin to accomplish a function of body strengthening. To improve the effect of fitness of negative-pressure cup, a negative-pressure cup may be added with a vibration box to provide vibration in the negative-pressure suction process. This can promote blood circulation and further enhance the effect of fitness.

Related-art negative-pressure cups have a certain function, but these products also have drawbacks of large volume, heavy weight or deviation on center of gravity, so they are not convenient in use. Some negative-pressure cups with a vibration function generate vibrational noise. For healthcare works and environment with long term use, noise obviously affects users so as to reduce the using willingness.

In view of this, the inventors have devoted themselves to the above-mentioned related art, researched intensively and cooperated with the application of science to try to solve the above-mentioned problems. Finally, the disclosure which is reasonable and effective to overcome the above drawbacks is provided.

SUMMARY

An object of the disclosure is to provide a negative-pressure cup structure with a vibration mechanism, which utilizes the firm connection of the vibration generating mechanism and the cup to sufficiently transfer vibration from the vibration generating mechanism to the cup so as to provide better vibrational sense for a user.

To accomplish the above object, the disclosure provides a negative-pressure cup structure with a vibration mechanism, which includes a cup and a vibration generating mechanism. The cup has a chamber. Two ends of the cup are separately formed with an opening end and a closed end. The closed end is provided with a negative-pressure suction hole and an electric connection hole communicating with the chamber. A bar is extended from the closed end and located in the chamber. The vibration generating mechanism includes a box, a vibration member disposed in the box and a power connector electrically connected to the vibration member. The vibration generating mechanism is fixed in the chamber of the cup in a manner of the box and the bar being connected and the power connector being inserted to the electric connection hole.

The disclosure further has the following functions. The box is placed at the center of the cup, so the center of gravity of the cup is not being deflected when the vibration member is operated. The vibrational sense with uniform forces may be achieved. The pad is disposed between the bar and the bar hole of the box base, so noise can be reduced. The box cover is extended with a protrusive ring around the button, so the button may be effectively prevented from being unexpectedly pressed in the operation process.

DETAILED DESCRIPTION

Figure 1:
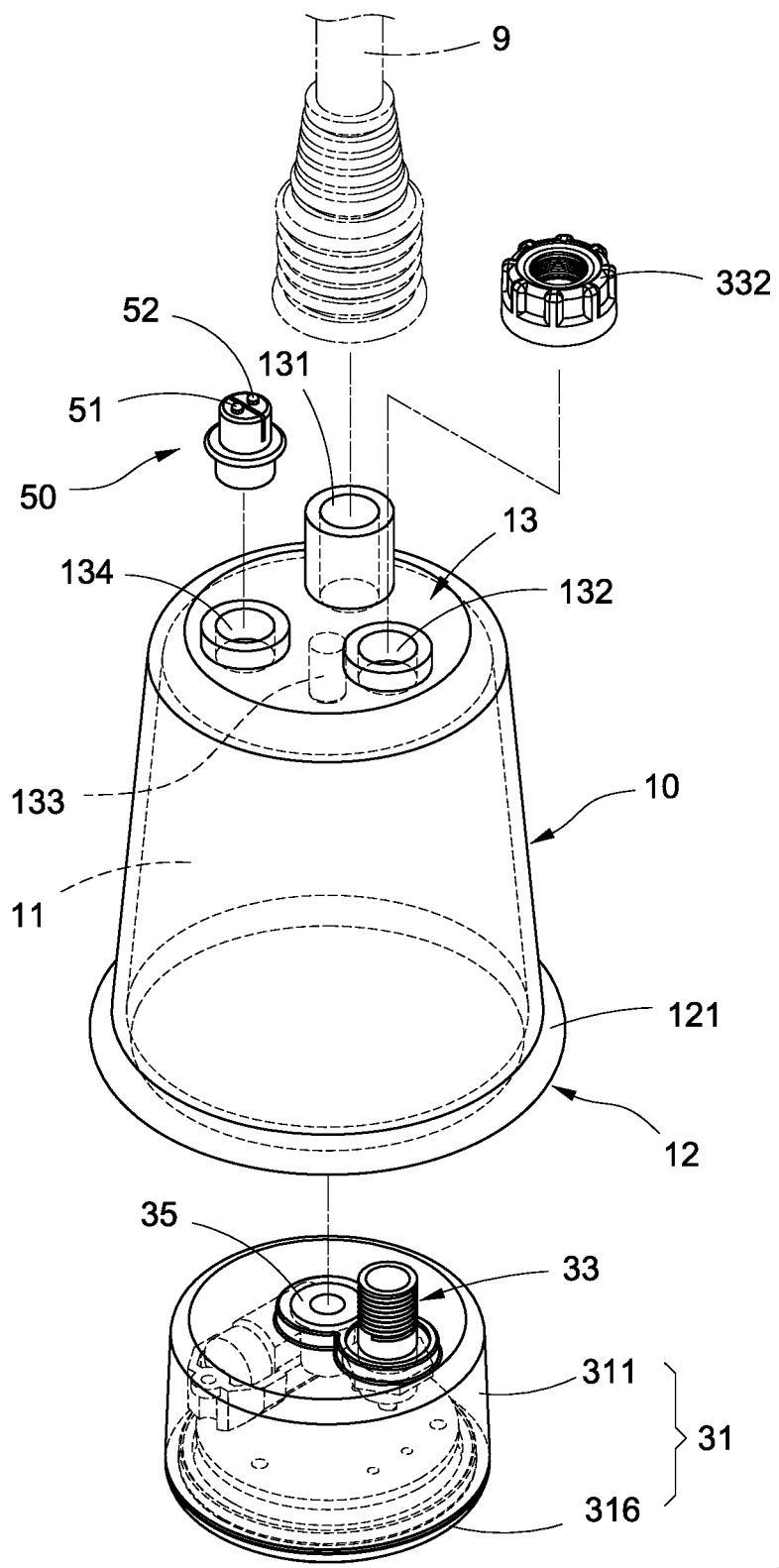
FIG. 1 is an exploded view of the negative-pressure cup structure with a vibration mechanism of the disclosure.
Figure 2:
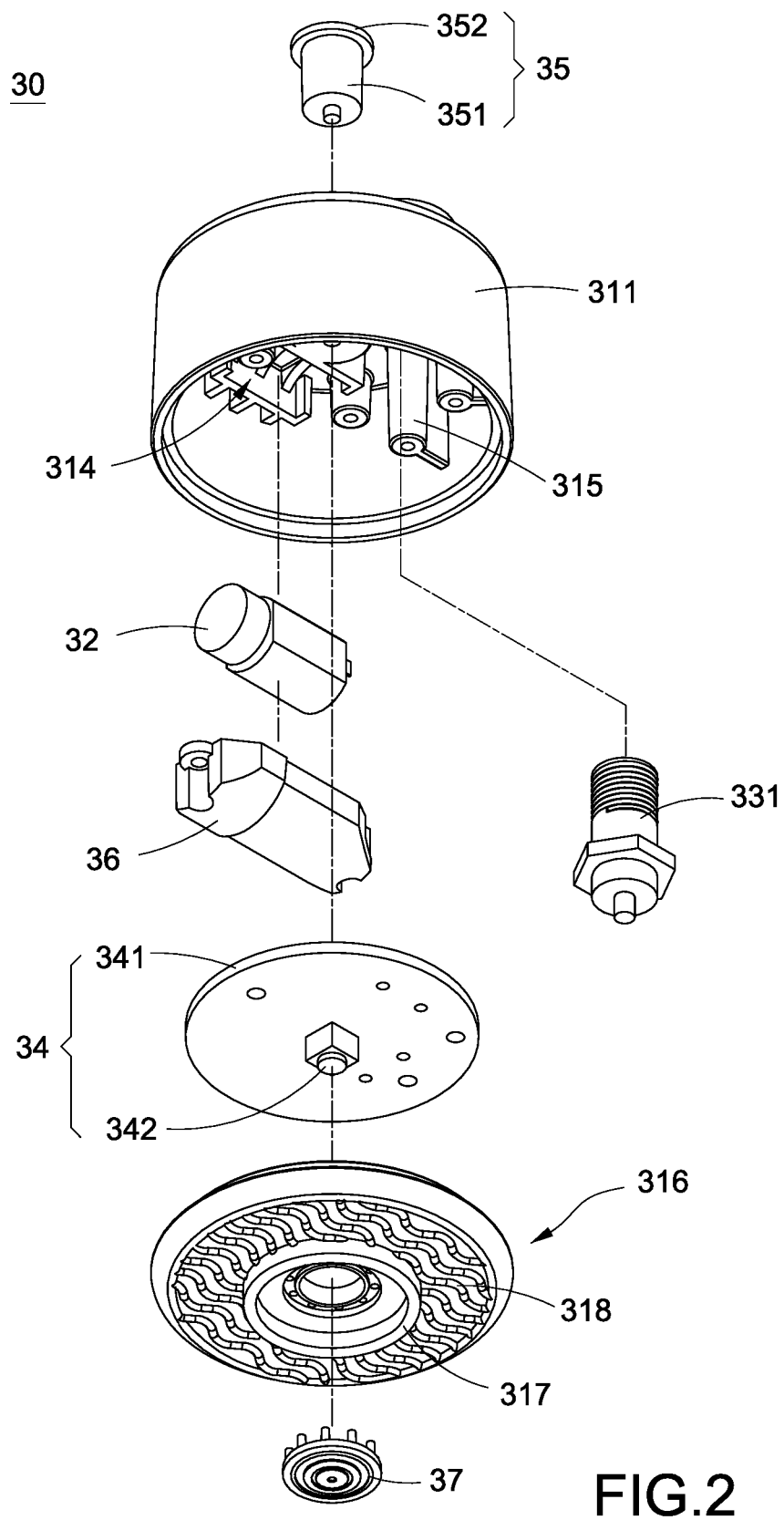
FIG. 2 is an exploded view of the vibration generating mechanism of the disclosure.
Figure 3:
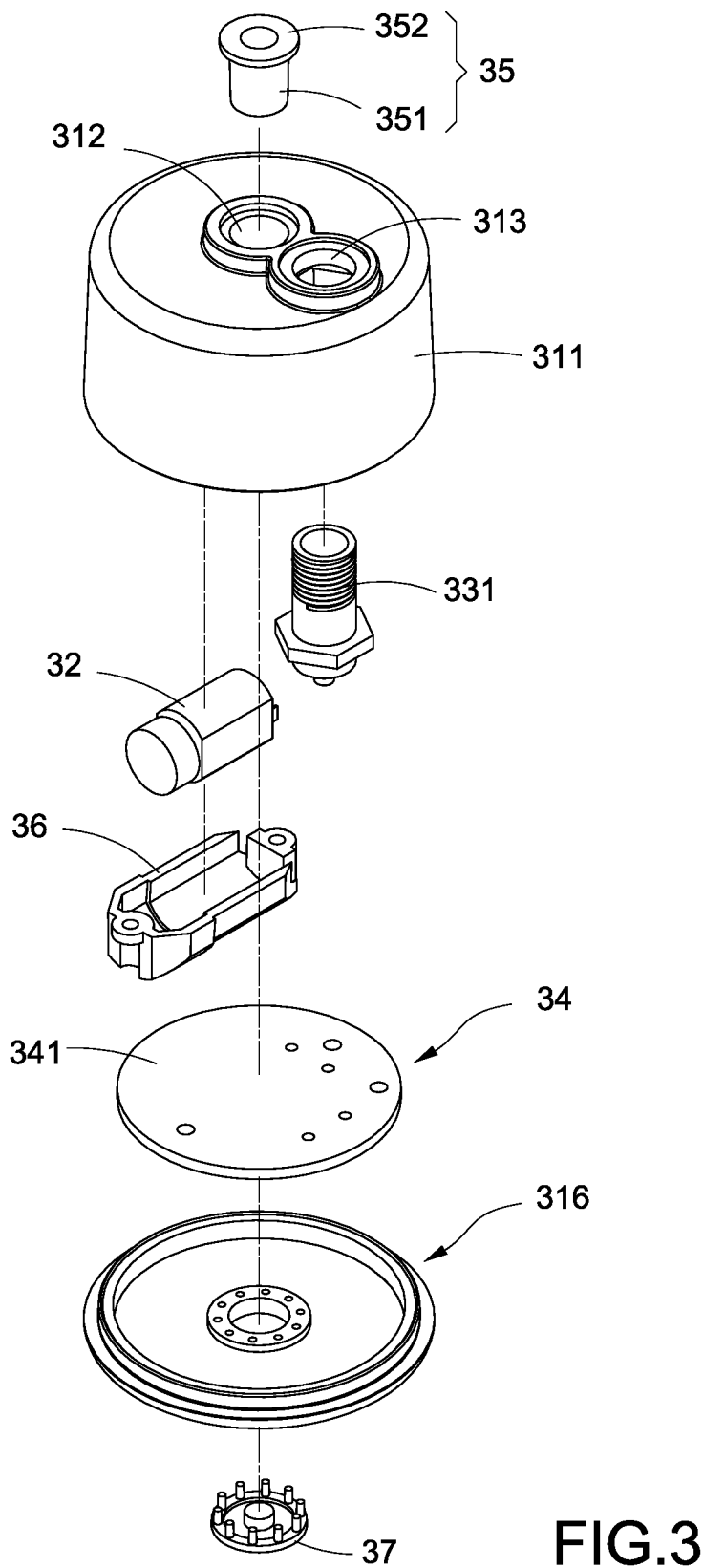
FIG. 3 is another exploded view of the vibration generating mechanism of the disclosure.
Figure 4:
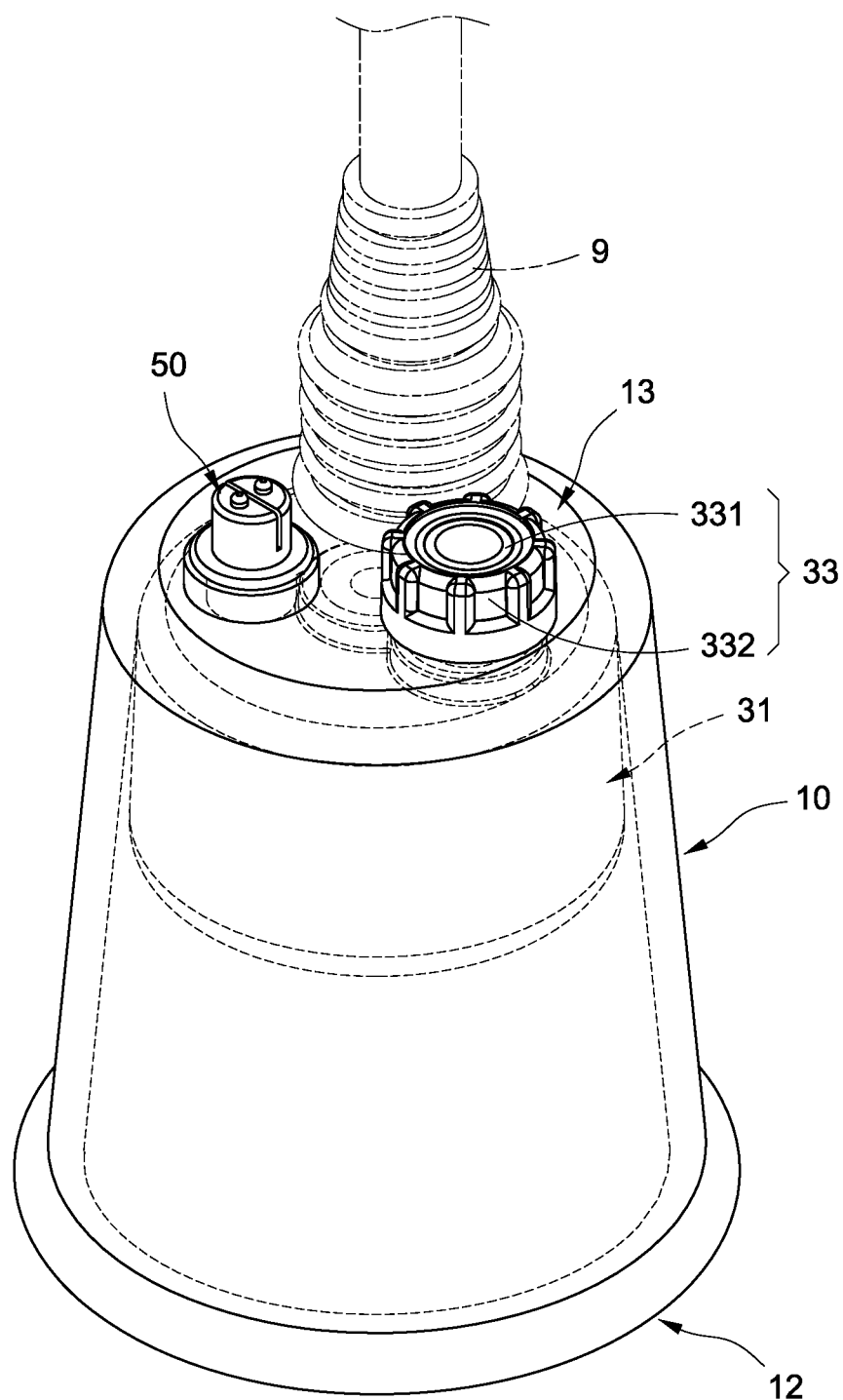
FIG. 4 is an assembled view of the vibration generating mechanism of the disclosure.

The technical contents of this disclosure will become apparent with the detailed description of embodiments accompanied with the illustration of related drawings as follows. It is intended that the embodiments and drawings disclosed herein are to be considered illustrative rather than restrictive.

Please refer to FIGS. 1-5. The disclosure provides a negative-pressure cup structure with a vibration mechanism, which includes a cup 10 and a vibration generating mechanism 30.

The cup 10 is approximately of a cylindrical shape and has a chamber 11. Two ends of the cup 10 are separately formed with an opening end 12 and a closed end 13. The closed end 13 is provided with a negative-pressure suction hole 131 and an electric connection hole 132. The negative-pressure suction hole 131 and the electric connection hole 132 communicate with the chamber 11. A bar 133 is extended from the closed end 13 and located at the center in the chamber 11. The negative-pressure suction hole 131 is used to provide the connection with a negative-pressure tube 9. A periphery of the opening end 12 is formed with an annular flange 121. The closed end 13 is provided with a plug hole 134 communicating with the chamber 11.

The vibration generating mechanism 30 includes a box 31, a vibration member 32 and a power connector 33. The box 31 includes a box base 311 and a box cover 316. The box base 311 is made of plastic material and approximately of a cylindrical shape. The center of the box base 311 is provided with a bar hole 312. A through hole 313 is formed on the box base 311 adjacent to the bar hole 312. The inside of the box base 311 is provided with a receiving room 314 for the vibration member 32 to be accommodated and fixed. A lateral side of the receiving room 314 is extended with multiple screw rods 315. The box cover 316 is also made of plastic material and correspondingly covers the box base 311. The box cover 316 and the box base 311 are connected in a welding manner so as to accomplish waterproof and dustproof effects.

The vibration member 32 of the embodiment is, but not limited to, a vibration motor. The frequency and vibrating level of the vibration member 32 may be varied depending on actual requirements to accomplish the vibrational senses in different degrees.

The power connector 33 includes a screw element 331 and a nut element 332. The screw element 331 passes the through hole 313 of the box base 311 and the electric connection hole 132 and is screwed with the nut element 332. The screw member 331 may be electrically connected to the vibration member 32 through a wire (not shown).

The vibration generating mechanism 30 is fixed in the chamber 11 of the cup 10 in a manner of the bar hole 312 of the box base 311 and the bar 133 being connected and the power connector 33 being inserted to the electric connection hole 132.

Furthermore, the vibration generating mechanism 30 further includes an electric assembly 34 including a circuit board 341, a switch 342 electrically connected to the circuit board 341 and other electric components. The circuit board 341 is fixed to the screw rods 315 by inserting fasteners such as screws. The vibration member 32 may be electrically connected to the circuit board 341 through a wire (not shown). The screw element 331 may also be electrically connected to the circuit board 341 through a wire (not shown). Thus, the vibration member 32 is switched on or off by pressing the switch 342.

Furthermore, the vibration generating mechanism 30 further includes a pad 35. The pad 35 may be made of soft material such as rubber or silicone and includes a cylindrical tube 351 and a flange 352 outward extended from an end of the cylindrical tube 351. The cylindrical tube 351 is tightly clamped between the bar 133 and the bar hole 312 of the box base 311. The flange 352 is clamped between the box base 311 and the closed end 13 of the cup 10. Thus, an effect of noise reduction can be accomplished.

Furthermore, the vibration generating mechanism 30 further includes a motor cover 36 which correspondingly covers the vibration member 32 and is fixed to the box base 311 through fasteners such as screws. Thus, the vibration member 32 is packaged in the receiving room 314 and the motor cover 36.

Furthermore, the vibration generating mechanism 30 further includes a button 37 disposed on the box cover 316 and arranged corresponding to the switch 342. The button 37 is pressed to trigger the switch 342 to response. The button 37 may be formed on the box cover 316 by secondary injection molding to accomplish a desirable effect of water resistance. The box cover 316 is extended with a protrusive ring 317 around the button 37. The protrusive ring 317 is higher than an outer surface of the button 37 (that is, an upper surface of the protrusive ring 317 is more protrusive than an outer surface of the button 37) to effectively prevent the button 37 from being unexpectedly pressed. Also, a surface of the box cover 316 is formed with multiple waved protrusive strips 318. The multiple waved protrusive strip 318 are arranged spacedly to form a gas channel between any two adjacent waved protrusive strips 318. That avoids a bruise caused by excessively adhesion between human skin and the box cover 316.

Furthermore, the negative-pressure cup structure with a vibration mechanism of the disclosure further includes a release member 50 arranged corresponding to the plug hole 134 of the cup 10. The center of the release member 50 is provided with a groove 51. Two sides of the groove 51 are respectively formed with a protrusive spot 52 on the release member 50. When using, the groove 51 may be opened by holding one of the protrusive spots 52 to allow air outside the cup 10 to enter the chamber 11 to release the negative pressure in the chamber 11 of the cup 10. When a user stops opening the groove 51, the groove 51 immediately returns to the original position to isolate air outside the cup 10 from air in the chamber 11.

Figure 5:
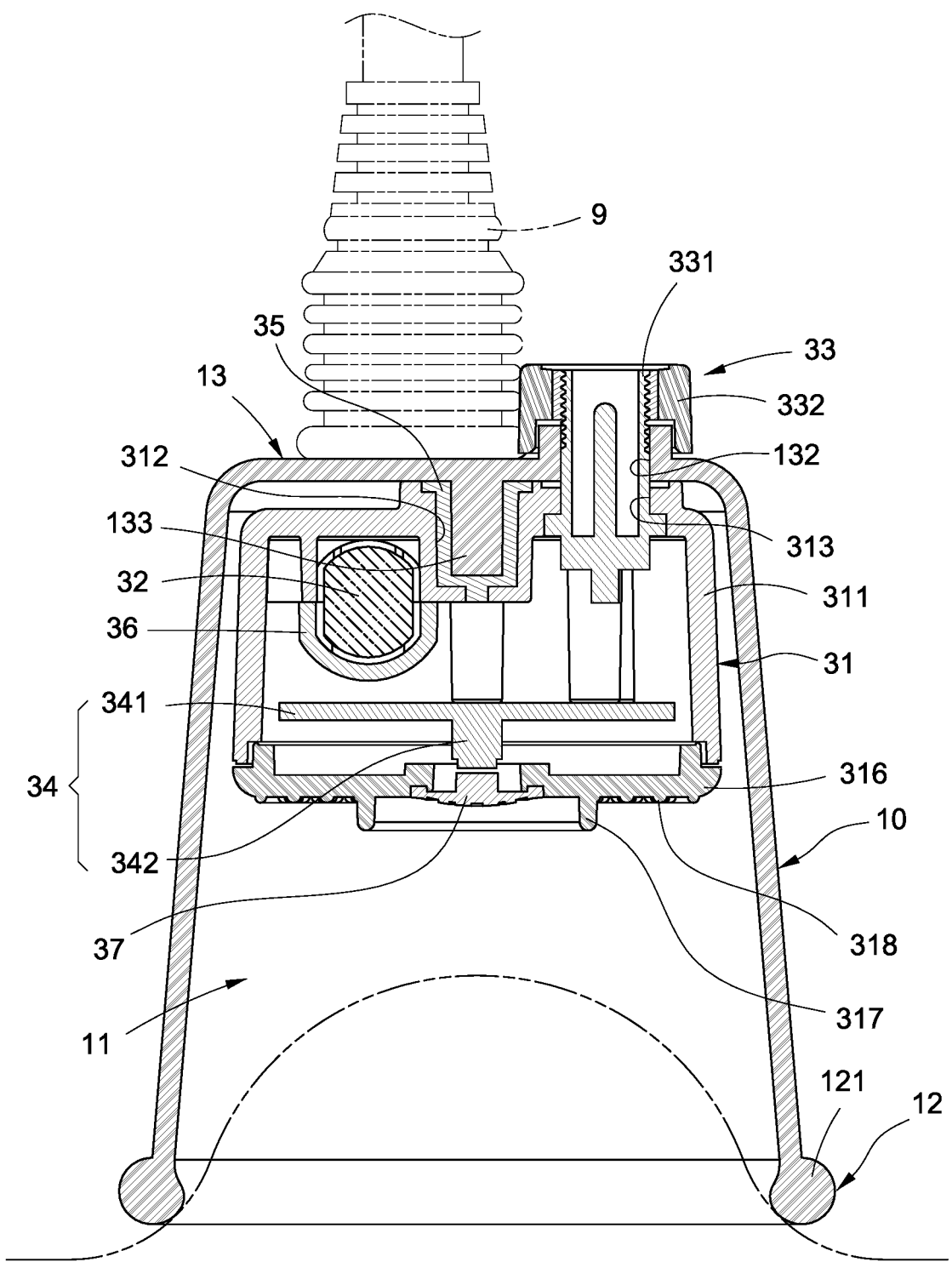
FIG. 5 is a cross-sectional view of the vibration generating mechanism of the disclosure.

Please refer to FIG. 5. When using, the opening end 12 of the cup 10 covers on human skin, air in the chamber 11 is sucked from the negative-pressure suction hole 131 through the negative-pressure tube 9 to generate negative pressure in the chamber 11 to make the covered skin swell (shown as the broken line in figure). Then, by the operation of the vibration generating mechanism 30, the effect of vibrational massage may be simultaneously obtained.

While this disclosure has been described by means of specific embodiments, numerous modifications and variations could be made thereto by those skilled in the art without departing from the scope and spirit of this disclosure set forth in the claims.

What is claimed is:

1. A negative-pressure cup structure comprising:
a cup, comprising a chamber, an opening end and a closed end disposed on two ends thereof separately, a negative-pressure suction hole and an electric connection hole disposed on the closed end and communicating with the chamber, and a bar extended from an inner surface of the closed end and located in the chamber; and
a vibration generating mechanism, comprising a pad, a box, a vibration member disposed in the box and a power connector being inserted to the electric connection hole to electrically connect to the vibration member, wherein the box comprises a box base and a box cover correspondingly covering the box base, a bar hole is disposed on a center of the box base and a through hole is disposed on the box base adjacent to the bar hole, the bar is inserted to the bar hole, the pad comprises a cylindrical tube clamped between the bar and the bar hole, the power connector comprises a screw element and a nut element, and the screw element passes the through hole and the electric connection hole to screw with the nut element.

2. The negative-pressure cup structure of claim 1, wherein the pad further comprises a flange outward extended from an end of the cylindrical tube, and the flange is clamped between the box base and the closed end.

3. The negative-pressure cup structure of claim 1, wherein the vibration generating mechanism further comprises a motor cover, a receiving room is disposed inside the box base to accommodate and fix the vibration member, and the motor cover correspondingly covers the vibration member and is fixed to the box base.

4. The negative-pressure cup structure of claim 1, wherein the vibration generating mechanism further comprises an electric assembly, multiple screw rods are extended inside the box base, the electric assembly comprises a circuit board fixed to the screw rods by multiple fasteners.

5. The negative-pressure cup structure of claim 4, wherein the vibration generating mechanism further comprises a button, the electric assembly further comprise a switch electrically connected to the circuit board, and the button is disposed on the box cover and arranged corresponding to the switch.

6. The negative-pressure cup structure of claim 5, wherein a protrusive ring is extended from the box cover on a periphery of the button, and an upper surface of the protrusive ring is more protrusive than an outer surface of the button.

7. The negative-pressure cup structure of claim 1, wherein the box cover is connected to the box base in a welding manner.

8. The negative-pressure cup structure of claim 1, further comprising: a release member, wherein a plug hole is disposed on the closed end and communicates with the chamber, and the release member is installed corresponding to the plug hole.

9. The negative-pressure cup structure of claim 8, wherein a groove is disposed on a center of the release member, and a protrusive spot is respectively disposed on two sides of the groove of the release member.

10. A negative-pressure cup structure comprising:
a cup, comprising a chamber, an opening end and a closed end disposed on two ends thereof separately, a negative-pressure suction hole and an electric connection hole disposed on the closed end and communicating with the chamber, and a bar extended from the closed end and located in the chamber; and
a vibration generating mechanism, comprising a box, a vibration member disposed in the box and a power connector electrically connected to the vibration member, the vibration generating mechanism is fixed in the chamber of the cup in a manner of the box and the bar being connected and the power connector being inserted to the electric connection hole,
wherein the box comprises a box cover, multiple waved protrusive strips are disposed on a surface of the box cover, and the multiple waved protrusive strips are arranged spacedly.

* * * * *